US011833238B2

(12) United States Patent
Corboy, Jr.

(10) Patent No.: US 11,833,238 B2
(45) Date of Patent: *Dec. 5, 2023

(54) TOPICAL TESTOSTERONE (T) FOR PROMOTING HAIR GROWTH-CONTAINING FORMULATIONS

(71) Applicant: Edward Dunne Corboy, Jr., Skokie, IL (US)

(72) Inventor: Edward Dunne Corboy, Jr., Skokie, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/333,964

(22) Filed: May 28, 2021

(65) Prior Publication Data

US 2022/0087918 A1 Mar. 24, 2022

Related U.S. Application Data

(63) Continuation of application No. 16/150,007, filed on Oct. 2, 2018, now Pat. No. 11,020,336, which is a continuation of application No. 15/970,339, filed on May 3, 2018, now Pat. No. 10,307,360, which is a continuation of application No. 13/986,854, filed on Jun. 12, 2013, now Pat. No. 9,987,213.

(60) Provisional application No. 61/689,808, filed on Jun. 13, 2012.

(51) Int. Cl.
| *A61K 8/63* | (2006.01) |
|---|---|
| *A61K 45/06* | (2006.01) |
| *A61K 8/42* | (2006.01) |
| *A61K 8/49* | (2006.01) |
| *A61Q 7/00* | (2006.01) |
| *A61K 31/568* | (2006.01) |
| *A61K 31/5575* | (2006.01) |

(52) U.S. Cl.
CPC .............. *A61K 8/63* (2013.01); *A61K 8/42* (2013.01); *A61K 8/4953* (2013.01); *A61K 31/5575* (2013.01); *A61K 31/568* (2013.01); *A61K 45/06* (2013.01); *A61Q 7/00* (2013.01)

(58) Field of Classification Search
CPC ............ A61K 2300/00; A61K 31/5575; A61K 31/568; A61K 45/06; A61K 8/42; A61K 8/4953; A61K 8/63; A61Q 7/00
See application file for complete search history.

(56) References Cited

U.S. PATENT DOCUMENTS

| 4,139,619 A | 2/1979 | Chidsey, III |
|---|---|---|
| 4,968,812 A | 11/1990 | Wang et al. |
| 5,607,978 A | 3/1997 | Woodward et al. |
| 6,262,105 B1 | 7/2001 | Johnstone |
| 2005/0025833 A1 | 2/2005 | Aschkenasy et al. |
| 2008/0070988 A1 | 3/2008 | Woodward et al. |
| 2010/0190853 A1 | 7/2010 | Rethore et al. |

FOREIGN PATENT DOCUMENTS

| CN | 101332171 A | 12/2008 |
|---|---|---|
| CN | 101332174 A | 12/2008 |

OTHER PUBLICATIONS

Kaufman et al., The Decline of Androgen Levels in Elderly Men and its Clinical and Therapeutic Implications. Endocrine Reviews. 2005; 26(6): 833-876.
Isaacs, Understanding Hormones, Weight, and Your Metabolism, book, published Nov. 1, 2006.
Hibino et al., Role of TGF-β2 in the human hair cycle. Journal of Dermatological Science. 2004; 35(1): 9-18.
Machine translation of CN101331174A, Dec. 31, 2008.
Thornton et al., Androgen-dependent beard dermal papilla cells secrete autocrine growth factor(s) in response to testosterone unlike scalp cells. J Invest Dermatol. Nov. 1998; 111(5): 727-32.
Ersatz, publicly available on Mar. 7, 2007.
Saeedi et al., A randomized, double-blind, controlled trial of testosterone gel treatment versus vehicle control on the facial hair of young men with beta-thalassemia major. J Dermatolog Treat. 2007; 18(5): 271-4.
Blogspot, http://beardgrowthexperiment.blogspot.com/, 2011.
Emails dated Aug. 3, 2016.
Farthing et al., Relationship between plasma testosterone and dihydrotestosterone concentrations and male facial hair growth. British Journal of Dermatology. Nov. 1982; 107(5): 559-564.
Chieffi, Effect of Testosterone Administration on the Beard Growth of Elderly Males. J Gerontol. Jul. 1949; 4(3): 200-4.
Rosenfield, Hirutism and the Variable Response of the Pilosebaceous Unit to Androgen. J Investig Dermatol Symp Proc. Dec. 2005; 10(3): 205-8.
Benzalkonium Chloride, Wikipedia.
Testosterone Propionate, Wikipedia.
Blade Shaving, Chapter 21. By Keith Ertel and Gillian McFeat, Cosmetic Dermatology, Products and Procedures, Edited by Zoe Draelos, M.D., Blackwell Publishing, Ltd. 2010; 156-163.
Ray A. Smith, The Struggle to Grow a Beard is Real, So Men Decide to Fake It—Eye Shadow, Fibers, Sprays create Full Facial Hair; the Rich Ross Look. The Wall Street Journal. Nov. 5, 2019.
Chang et al., Generic Development of Topical Dermatologic Products: Formulation Development, Process Development, and Testing of Topical Dermatologic Products. The AAPS Journal. Jan. 2013; 15(1): 41-52.
Grow Body Hair, Increase DHT?, MindandMuscle.com. 2007.
Harman et al., Longitudinal Effects of Aging on Serum Total and Free Testosterone Levels in Healthy Men, The Journal of Clinical Endocrinology & Metabolism. Feb. 2001; 86(2): 724-31.

(Continued)

*Primary Examiner* — Jean P Cornet
(74) *Attorney, Agent, or Firm* — McAndrews, Held & Malloy, Ltd.

(57) ABSTRACT

The present invention relates to the composition and method of use for the topical application of the potent androgen hormone dihydrotestosterone (DHT), used alone or in fixed combination with other hair growth medications; including other androgens, bimatoprost, other prostamides, prostaglandins, minoxidil or apocrine hair growth factors to promote and enhance hair growth of terminal mustache hair, beard hair, also chest hair, and other male androgen sensitive or dependent hair growth in humans or animals.

15 Claims, No Drawings

(56) References Cited

OTHER PUBLICATIONS

"5-alpha reductase deficiency," Web page <https://rarediseases.info.nih.gov/diseases/5680/5-alpha-reductase-deficiency> Last updated: Dec. 2, 2011; 4 pages, retrieved Feb. 11, 2021.
"Partial androgen insensitivity syndrome," Web page <https://rarediseases.info.nih.gov/diseases/5692/partial-androgen-insensitivity-syndrome> Last updated: Oct. 16, 2013; 5 pages, retrieved Feb. 11, 2021.
Azziz et al., Endocrine Reviews 21(4): 347-362, 2000.
Price et al., J. Clin. Invest. 1984; 74(4): 1496-1508, 1984.
Brunton, L.B., Lazo, J.S., & Parker, K.L. (Eds.). (2006) Goodman & Gilman's The Pharmacological Basis of Therapeutics. (11th ed.). New York: McGraw-Hill. pp. 1573-1585.

TOPICAL TESTOSTERONE (T) FOR PROMOTING HAIR GROWTH-CONTAINING FORMULATIONS

CROSS-REFERENCE TO RELATED APPLICATIONS/INCORPORATION BY REFERENCE

The present application is a continuation of U.S. patent application Ser. No. 16/150,007, filed Oct. 2, 2018, now allowed, which is a continuation of U.S. patent application Ser. No. 15/970,339, filed May 3, 2018, now issued as U.S. Pat. No. 10,307,360 on Jun. 4, 2019, which is a continuation of U.S. patent application Ser. No. 13/986,854, filed Jun. 12, 2013, now issued as U.S. Pat. No. 9,987,213 on Jun. 5, 2018, which claims priority to and the benefit of U.S. Patent Application No. 61/689,808, filed Jun. 13, 2012. The above-identified applications are hereby incorporated herein by reference in their entirety.

BACKGROUND OF THE INVENTION

This invention seeks to solve the problem faced by many men have with weak mustaches and/or weak beard hair growth and/or weak chest hair growth by providing for the topical application of dihydrotestosterone (DHT), used alone or in fixed combination with other hair growth medications; including other androgens, bimatoprost, other prostamides, prostaglandins, minoxidil or apocrine hair growth factors to promote and enhance hair growth of terminal mustache hair, beard hair, also chest hair, and other male androgen sensitive or dependent hair growth in humans or animals.

This invention may make it possible for some men to bypass and overcome their own hair follicle genetic limitations (as its relates to the levels of intracellular 5 alpha reductase, and also, the number of androgen receptors located inside the mesenchymal dermal papilla cells in the hair follicles of the mustache, beard and chest hair areas). This invention can thus lead to more full, thick, virile, more pigmented and robust hair growth of terminal hairs in the mustache, beard and chest areas in some men.

The inventor is not aware of any U.S. Food and Drug Administration medications approved for the indication of promoting facial hair growth in the mustache or beard areas. Nor is he aware of any U.S. Food and Drug Administration medications approved to promote the growth of androgen sensitive or androgen dependent hair growth on the chest or other parts of the body.

The inventor is unaware of any patented methods for using pharmaceuticals, medications or other synthetic or naturally occurring compounds, approved to promote and enhance the growth of mature, terminal facial hairs in the mustache or beard areas. The same is true for chest hair growth or other areas of androgen dependent hair growth.

This composition and method uses the topical application of dihydrotestosterone (DHT), used alone or in fixed combination with other hair growth medications; including other androgens, bimatoprost, prostamides, prostaglandins, minoxidil or apocrine hair growth factors to promote and enhance hair growth of terminal mustache hair, beard hair, chest hair, and other male androgen sensitive or dependent hair growth in humans or animals, utilizing liquids, lotions, ointments, creams, gels, foams, sprays or aerosols or other solvents.

This invention addresses a long felt, but unmet need. For many decades, young adult men and adult men have been well aware of there lack of ability to grow strong, full and robust mustache, beard and chest hair. There have been no scientific or pharmaceutical options available to them until now.

At birth, the average healthy human is born with 5 million hair follicles on the body. Of these, 1 million hair follicles are located on the head, with 100 thousand hair follicles located on the scalp area. Of note, scalp hair follicles, as well as eyebrow and eyelash hair follicles are not dependent on androgen hormones to produce hair growth. After birth, no new hair follicles are created on the human skin.

All hair, both human and animal, passes through a life cycle that includes three phases, namely, (1) the anagen phase (2) the catagen phase and (3) the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one begins to grow.

Now, under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

The skin is a multifunctional and multicompartment organ affected by diseases and their treatments. The bulk of percutaneous absorption of most agents is through the stratum corneum, which covers the entire skin surface. Of note, hair follicles and hair shafts can also play an important role in absorbing topical medications and compounds applied to the surface of the skin. Epidermal structure and sweat glands are also potential pathways of absorption of topically applied medications or hair growth agents. Hair follicles form a lipid-rich pathway for drug absorption and also represent a special shunt pathway to allow for a direct pathway for topical medications to reach key hair follicle structures and also provides a localized drug reservoir that can enhance local effects of medicines in the hair follicles. The absorption of drugs and chemicals into and onto hair shafts also can be used to measure prior drug exposure.

TECHNICAL FIELD OF THE INVENTION

The technical field of this invention relates to the topical use of the potent androgen, dihydrotestosterone (DHT), used alone or in fixed combination with other hair growth medications; including other androgens, bimatoprost, prostamides, prostaglandins, minoxidil or apocrine hair growth factors to promote and enhance hair growth of terminal mustache hair, beard hair, also chest hair, and other male androgen sensitive or dependent hair growth in humans or animals.

The role of dihydrotestosterone (DHT) in specific hair follicle cellular activity located in the mustache, beard, chest and androgen dependent hair follicles is well known. Both dihydrotestosterone (DHT) and testosterone (T) are known to play an important role in the cell biology of mesenchymal dermal papilla cells located in the bulbs of androgen dependent hair follicles. Once dihydrotestosterone (DHT) and testosterone (T) are engaged with androgen receptors in these dermal papilla cells, they migrate into the nucleus of the cell and trigger and expression of genetic coding that leads to the creation of many apocrine growth factors and other hair growth factors that lead to mature terminal hair growth in androgen dependent hair follicles.

Some scientists suggest that there are basically two types of hair, soft lanugo hair called vellus hair, and a thicker, coarser hair called a terminal hair. Vellus hair is all over the body except for the palms and soles. Hair growth can be further differentiated as being either androgen dependent or androgen independent hair. This distinction becomes important during puberty and throughout adulthood. Other scientists have noted an intermediate type of hair that is on the continuum between vellus hair and terminal hair.

Hair growth on the scalp is not dependent on androgen hormones. However, hair loss on the scalp leading to male or female pattern hair loss is often related to both genetics and the effects of testosterone (T) and dihydrotestosterone (DHT) (as well as other factors) that lead to the loss of active scalp hair follicles that can produce either vellus or terminal hairs.

Hair growth of eyelash hair or eyebrow hair is not androgen dependent. As with scalp hair, young children with normal health are usually able to grow scalp hair, eyelash hair and eyebrow hair before puberty.

In the epidermis, the stratum corneum is the outer layer and is 5-600 microns thick. The stratum corneum is the major barrier to percutaneous absorption of drugs and also helps minimize the loss of water from the body. It is made of "dead" epidermal cells that cannot reproduce and have lost their nuclei and mitochondria. It possesses multiple proteins and lipids that may reversibly or irreversibly bind drugs. Many chemicals and physical treatments to enhance percutaneous absorption work within the stratum corneum. Many drugs may partition into the stratum corneum and can function as a reservoir for drugs that will diffuse into the rest of the skin, even after topical application of the drug has ceased. The stratum corneum varies in thickness. Facial and post auricular have the thinnest stratum corneum.

The living layers of the epidermis with metabolically active cells comprise a layer of ~100 microns thick. The lowest or basal layer of the epidermis is called the stratum basale and is responsible for the bulk of cell division. Several cell layers in the spinous layer (stratum spinosum) contain cells that actively synthesize most epidermal proteins, especially keratins. The uppermost layer of the living epidermis is the stratum granulosum. This layer is where extracellular lipids are extruded from the epidermis.

There is a superficial capillary plexus of blood vessels between the dermis and epidermis that is the site of the majority of the systemic absorption of cutaneous drugs. There are a large number of lymphatics as well in this area.

The dermis is about 1,200 microns thick that is in part composed of collagen and proteoglycans that may bind drugs. Below the dermis, is a subcutaneous tissue called the hypodermis.

The hair shaft is formed by keratinized cells containing highly organized material. Hair has the appearance of an extremely elongated cylinder. The hair shaft has three (3) regions: The cuticle, the cortex and the medulla found close to the center of the hair shaft.

Lanugo hairs, the first body hairs formed in the embryo, are vellus in character, but often longer than the vellus shafts of the adult. The vellus hair shaft is short, thin, fine, lightly pigmented, and with no medulla. A vellus hair follicle is defined as a small follicle that extends no deeper than the upper dermis and produces a shaft no wider than its internal root sheath. Although vellus follicles may lack arrector pili muscles in some areas, vellus hair follicles are associated with these structures on the face. With maturity and exposure to androgens, regional human hair follicles switch in morphology to terminal follicles that produce terminal hair shafts. The inverse terminal-to-vellus switch occurs on the scalp of the genetically susceptible androgenic alopecia individuals after exposure to androgens.

The hair cycle appears to he central to the vellus-to-terminal hair follicle switch because phenomenologically the cycle appears to initiate that process; the follicle must cycle in order for the switch to occur. We do not yet know how the cycle is related to this transformation, although it may be due to a gradual change in the size of the papilla with the completion of each cycle. Relatively little attention has been given to this switch phenomenon mechanistically; in fact, even the follicle that characteristically switches has not yet been fully characterized.

The wide response range of hair to androgens reflects inherent genetic differences of hair depending on body site. There is a graded response of regional hairs to androgen levels; inguinal and axillary follicles, for example, are stimulated to grow under low levels of androgen, and facial hair to high levels, while deep temporal/occipital scalp and eyebrow/eyelash hair are insensitive o androgen levels altogether. This principle underlies the success of scalp hair transplants for male pattern balding, where androgen-insensitive hairs (occipital area) are transplanted to sites of androgen-sensitive hairs (frontal, parietal, coronal areas). Thus one must distinguish between hairs that are androgen dependent (axilla, mustache, beard and chest), androgen insensitive (eyebrow and eyelash), and androgen independent but androgen sensitive (scalp vertex in susceptible individuals). Ultimately, these interfollicular and interregional differences must stem from the way a given follicle is genetically programmed and how it responds to androgen stimulation, its androgen target genes, and the nature of its androgen receptor-mediated signal transduction events. Unfortunately, these parameters have not yet been dissected.

Hair growth during and after puberty of mature terminal hairs on the face in the mustache and beard areas is androgen dependent. The same is true for terminal hair growth in the chest and other parts of the male body. This process begins in puberty in boy who are developing secondary sex characteristics on their way to becoming young adult men.

Hair biology and hair loss physiology are complex and relate to a wide range of genetic variables, ethnic background, family history & genetics, health status, medication use, diet and even psychosocial stress levels.

The exploration and investigation of possible treatment options for treating and promotion hair growth in men who have weak, sparse or inconsistent mustache, beard, chest and other androgen dependent hair growth areas requires an in depth understanding of hair biology, endocrinology, genetic hair growth variables in both sexes, and hormonal regulation of hair growth factors in different areas of the skin.

Genetics plays an important role both in the density and number of hair follicles in the mustache, beard and chest hair areas. In addition, genetics may determine the number of androgen receptors located in individual hair follicle cells on the face and chest. Further, genetics helps to determine the level and activity of the enzymes 5 alpha reductase 1, 2 and 3 that play an important role within the body and also in the hair follicle cells relating to the growth of mature terminal facial hair, mustache hair, beard hair, chest hair and other androgen dependent hair growth.

Ethnic origin and ancestry can play an important role and have a great impact on the hair growth in men. This is true for facial hair growth, chest hair growth, scalp hair growth and hair growth on the entire body.

For young men and adult men who are unable to grow robust and full beards and mustaches, this may be related to a lack of adequate numbers of androgen receptors in hair follicle cells in the mustache, beard and chest hair areas. In addition, this problem may also be related to a genetically determined lower level of intracellular 5 alpha reductase enzymes 1, 2 and 3 levels within hair follicle cells in the mustache, beard and chest hair areas.

It is well established that testosterone and dihydrotestosterone play key roles in the development of classic male secondary sex characteristics that promotes the virilization of adolescent boys to mature adult men during adolescence and sexual maturation. In addition, both testosterone and dihydrotestosterone play important roles in developing fetuses, children during adolescence, early adulthood and throughout life in both male and female humans. This is also true for animals.

All naturally occurring androgens play a critical role in human health and all androgens have major conversions and important metabolic pathways for interconversion into other hormones, other steroid hormones and other sex hormones. The same is true for animals.

It is well known that at the cellular level, testosterone is routinely converted into to dihydrotestosterone via the enzymes five alpha reductase 1, 2 and 3. This conversion of testosterone to dihydrotestosterone within hair follicles, that usually happens within cells, creates a very powerful anabolic androgenic steroid hormone, dihydrotestosterone (DHT), that is 2 to 5 times more potent and powerful than testosterone in causing a wide range of physiologic effects in the body. This is particularly true with regard to androgen dependent hair growth in the human body compared to testosterone. The same is true in animals.

It is known that dihydrotestosterone (DHT) binds more tightly to the androgen receptors located in cells in many parts of the body relating to male hair growth than does testosterone (T). The conversion of testosterone (T) to dihydrotestosterone (DHT) results in an amplification the physiologic effect of testosterone (T) with regard to facial hair growth and chest hair growth.

While this patent application addresses the problem of weak, sparse or inconsistent hair growth in the mustache, beard, chest and other androgen dependent hair growth, for the most part, the vast majority of research in hair biology has centered on male and female loss of hair or baldness. A great deal of scientific effort and hard work has investigated a wide number of ways to deal with both male and female hair loss on the scalp. The enormity of the emotional pain and suffering, the sense of lost youth, lost identity, and lost physical and sexual attractiveness caused by the loss of, or the thinning of scalp hair, in both men and women is beyond calculation. Genetics plays a key role in determining what males and females will be impacted by mild, moderate and severe hair loss in the scalp area over their lifetimes. The complex nature of hair genetics and hair biology relating to scalp hair loss is most interesting and scientists have made some early and significant strides in understanding the key roles of many factors relating to hair loss, hair growth and hair characteristics. Major pharmaceutical companies have invested in serious hair biology research related to loss of hair on the scalp. Sales of medications for reversing or slowing down human scalp hair loss have provided some men and women with improved scalp hair growth and also generated significant sales and profits. Such scientific insights have included the important roles of androgens [in particular dihydrotestosterone (DHT) and testosterone (T)] as well as the role of the 5 alpha reductase enzymes play in leading to the loss of scalp hairs and sometimes major hair loss on the scalp leading to significant baldness and at times the complete destruction of hair follicles in the scalp.

However, little to no attention has been paid to the longstanding problem of weak, sparse or less than robust facial hair growth in the mustache and beard areas. While for some young adult men and adult males, mustache and beard growth is strong and impressive, there are many young men and adult men who are not able to grow a full beard and/or a full, thick and strong mustache. This is related to genetics, specific hair follicles genetics, and a host of other factors outside a person's control. Maturing boys, young men and adult men learn on their own accord as they move through puberty into early adulthood if they are able to grow both a full, thick and strong beard and mustache. Those who find that they are unable to grow a full, thick and consistently strong mustache, and who would like to grow a mustache, have had no real medical treatment options to enhance their potential for improving their own ability to grow a full and more robust mustache. The same is true for men who find that they have only been able to grow weak or spotty beards.

It is of great interest to note that some men are able to grow fairly full and strong beards, yet are unable to grow a full, thick and strong mustache. Many men are unable to grow a full, rich and robust mustache, beard and chest hair. This is related to their genetics, the hair biology of key hair follicles in the mustache, beard and chest hair areas. This is well demonstrated when one observes professional hockey players and football players who often do not shave during playoffs games or championship playoff series. These professional athletes often put on their "game faces" on and do not shave there mustache or beard areas to appear more tough and intimidating. When watching these exceptional athletes, it is clear that some players are able to grow full mustaches and beards. Yet others are often unable to grow strong and full mustache hair and/or beard hair. It is quite striking to see how many professional hockey players and football players are unable to grow full, thick and robust mustache hair and beard hair. Some grow very weak and sparse mustache and beard hair. Clearly these elite professional male athletes have normal or high normal levels of circulating testosterone. This is just an example of what may be going on a large scale basis for men between the ages of 18 to 65.

While the hair follicles in the beard area and mustache area are exposed to the same levels of circulating androgen hormones [particularly testosterone (T) and dihydrotestosterone (DHT)] in males, in some men, the growth of a mustache hair never quite comes up to the level of full and consistently thick hair growth that occurs in the beard area. Some might designate these men as having "weak mustache hair growth syndrome" ("WMHGS"). The same is true for chest hair and for other areas of the skin where male secondary sex characteristics relating to body hair growth and appearance are well described.

SUMMARY OF THE INVENTION

In its most broad embodiment, the invention is a compound and method for promoting and enhancing the growth of androgen sensitive or androgen dependent hair in areas of human skin sensitive to or dependent on androgen for growth of hair, comprising the steps of applying a topical pharmaceutically acceptable formulation of dihydrotestosterone (DHT), used alone or in fixed combination with other hair growth medications; including other androgens, bimatoprost, prostamides, prostaglandins, minoxidil or apocrine hair growth factors to promote and enhance hair growth of terminal mustache hair, beard hair, also chest hair, and other male androgen sensitive or dependent hair growth in humans or animals. The invention is applied in a topical manner to targeted skin areas where hair growth is desired and regularly repeating said application until desired hair growth results. This includes areas in the region of mustache hair growth, beard hair growth, or chest hair growth.

The composition and method includes the use of dihydrotestosterone (DHT) as a topical monotherapy for the promotion and enhancement of mustache, beard, chest hair and other androgen dependent hair. The topical composition of dihydrotestosterone (DHT) may be of the 1% to 25%. The composition and method includes the topical application of such formulations to adolescents or adults.

The dihydrotestosterone (DHT) topical formulations used in the method of the invention additionally comprises one or more additional other androgens, for example testosterone (T), 1 to 25%, or can additionally comprise one or more non-steroidal alopecia treatment agents, for example minoxidil, 2% to 5% w/v, or one or more hair growth promoters including prostamindes or prostaglandins, further including travoprost, latanoprost or bimatoprost 0.001% to 0.1% w/v and most preferably 0.03% w/v. These formulations can be administered as topical lotions, ointments, solutions, gels, foams, or sprays. The topical formulations are formulated so as to deliver the active ingredient(s) to the hair follicles and the bulb matrices of hair follicles, or to the mesenchymal dermal papilla cells of the hair follicles and also hair follicle structures that can be reservoirs for applied formulations.

The inventor believes that it is most useful to formulate the topical formulation so as to he able to be absorbed into the hair follicle structures in a targeted manner. In addition, to allow the formulation to also adsorb onto a hair shaft itself and be drawn by, capillary action to the target hair follicle bulb and other hair follicle structures. Additional useful formulation properties are the ability to cross the surface of the skin and travel to the hair follicle bulb matrix by trans-epidermal diffusion or by transdermal diffusion, following Fickes' laws of diffusion. This is beneficially accomplished by the addition of one or more dermal penetration enhancement agents, such as a lower alcohol, including methanol, ethanol, propanol, or isopropanol.

The most preferred embodiments of the invention utilize topical formulations that cause the active ingredient(s) to penetrate the layers of the epidermis and dermis sufficiently to reach the hair follicles and the hair follicle bulb matrices, but not of such a great concentration so as to be absorbed to a significant degree into the systemic circulation.

Most preferred concentrations of dihydrotestosterone (DHT) run in a range of from about 0.5% to about 25%, measured w/w, /w/v, or v/v. Additional topical formulation ingredients include pharmaceutically acceptable preservatives such as benzalkonium chloride, 0.2 to 0.5 mg/mL, sodium chloride, dibasic sodium phosphate, citric acid, and pharmaceutically acceptable purified water, eg. distilled water, reverse osmosis water, and so on. An important aspect of the present invention is that a topical formulation can contain dihydrotestosterone as a monotherapy or in any fixed dose combination with one or more of testosterone, minoxidil, the prostamide bimatoprost, other prostamides and prostaglandin analogs, including travoprost, or latanoprost.

DETAILED DESCRIPTION OF THE DRAWINGS

No drawings or FIGURES are presented.

DETAILED DESCRIPTION OF THE INVENTION

This method of use pharmaceutical invention relates to the topical use of the potent androgen dihydrotestosterone (DHT), used alone or in fixed combination with other hair growth medications; including other androgens, bimatoprost, other prostamides, prostaglandins, minoxidil or apocrine hair growth factors to promote and enhance hair growth of terminal mustache hair, beard hair, also chest hair, and other male androgen sensitive or dependent hair growth in humans or animals.

This invention seeks to solve the problem faced by many men have with weak mustaches and/or weak beard hair growth and/or weak chest hair growth by providing for the topical application of dihydrotestosterone (DHT), used alone or in fixed combination with other hair growth medications; including other androgens, bimatoprost, other prostamides, prostaglandins, minoxidil or apocrine hair growth factors to promote and enhance hair growth of terminal mustache hair, beard hair, also chest hair, and other male androgen sensitive or dependent hair growth in humans or animals.

This invention may make it possible for some men to bypass and overcome their own hair follicle genetic limitations (as its relates to the levels of hair follicle intracellular 5 alpha reductase enzyme levels & activity, and also, the number of androgen receptors located inside the mesenchymal dermal papilla cells in the hair follicles of the mustache, beard and chest hair areas). This invention can thus lead to more full, thick, dense, virile, more pigmented and robust hair growth of intermediate and/or terminal hairs in the mustache, beard and chest areas in some men.

For many men who are unable to grow a consistently full beard and/or a consistently full and robust mustache, it may be due to the possibility that the underlying problem relates to a lack of, or a lack of full expression of, the genetically programmed enzyme, 5 alpha reductase that exists in mesenchymal dermal papilla cells, which are located in the dermal bulb areas of the deepest part of the hair follicles located in the mustache, beard and chest hair areas of the human body.

In addition, for some men, the number genetically programmed numbers of androgen receptors that are located in the mesenchymal dermal papilla cells located at the base of the hair follicles in the mustache, beard and chest areas may be decreased compared to other areas where beard, mustache and chest hair growth is more active and full.

In androgen dependent hair follicles on the mustache, beard and chest hair areas, a critical conversion of testosterone (T) to dihydrotestosterone (DHT) occurs due to the enzyme 5 alpha reductase. The 5 alpha reductase enzymes located with the hair follicles and the mesenchymal dermal papilla cells in the hair follicles allow for testosterone to be converted into a more potent androgen hormone, dihydrotestosterone, that can play a more powerful role in promotion hair growth activity in androgen dependent hair follicles located in the mustache, beard, chest and other parts of the body.

This invention allows for the topical application of the potent androgen, dihydrotestosterone (DHT), directly to skin surface and allows for the dihydrotestosterone (DHT) to reach the hair follicle structures and the mesenchymal dermal papilla hair follicle cells located in the hair bulb via the hair shaft, the hair follicle and the skin and lead to the increased production of mature, terminal mustache, beard and chest hair growth.

For the first time, there may now exist a topical pharmaceutical therapy (and also fixed combination therapies) that can overcome the limitations of genetic programming of important androgen dependent hair follicles in the mustache, beard, chest and other androgen dependent hair growth areas. This is accomplished through the use of dihydrotestosterone (DHT) in a topical manner, used alone or in fixed combination with other hair growth medications; including other androgens, bimatoprost, other prostamides, prostaglandins, minoxidil or apocrine hair growth factors to promote and enhance hair growth of terminal mustache hair, beard hair, also chest hair, and other male androgen sensitive or dependent hair growth in humans or animals.

This targeted delivery of dihydrotestosterone (DHT), used alone or in combination with other androgens, does not seek to achieve complete transdermal penetration of medication into the subcutaneous fat layer located beneath the dermis. The present invention seeks to achieve targeted delivery of dihydrotestosterone (DHT) to the hair follicle bulbs and mesenchymal dermal papilla cells with minimal drug reaching the systemic circulation. This mitigates against systemic absorptions of the drug and reduces the possibility of adverse hair loss events in the scalp hair area and also mitigates against any significant elevation of systemic dihydrotestosterone (DHT) levels that could lead to prostate hyperplasia or cancer.

It may be possible that the use of targeted and topical dihydrotestosterone (DHT) is only necessary for a period of a few weeks or months to sufficiently activate, trigger and transform vellus hair follicles to more mature terminal hair follicles and lead to the production of mature, terminal hairs in the mustache, beard and chest areas so as to be a short term therapy that leads to long term results. This is called a transformation of a vellus hair follicle to a terminal hair follicle that may continue on long after the initial application of the dihydrotestosterone (DHT).

While the present invention may be embodied in many different forms, several specific embodiments are discussed herein with the understanding that the present disclosure is to be considered only as an exemplification of the principles of the invention, and it is not intended to limit the invention to the embodiments illustrated. Where the invention is illustrated herein with particular reference to dihydrotestosterone (DHT), it will be understood to those skilled in the art that any other androgen can, if desired, be substituted in whole or in part for dihydrotestosterone (DHT) in the methods herein described.

In one embodiment, the present invention is directed to a method for topical administration of dihydrotestosterone (DHT) in a liquid. The liquid comprises dihydrotestosterone (DHT), used alone or in combination with another androgen, that would he applied to the outer surface of skin areas where a person would hope to increase facial hair growth in the mustache of beard areas, or in the chest area. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

In another embodiment, the present invention is directed to a method for topical administration of dihydrotestosterone (DHT) in a lotion. The lotion comprises dihydrotestosterone (DHT), used alone or in fixed combination with other hair growth medications; including other androgens, bimatoprost, prostamides, prostaglandins, minoxidil or apocrine hair growth factors to promote and enhance hair growth of terminal mustache hair, beard hair, also chest hair, and other androgen sensitive or dependent hair growth in humans or animals that would be applied to the outer surface of skin areas where a person would hope to increase facial hair growth in the mustache of beard areas, or in the chest area. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

Other embodiments of this invention are directed to a method for optical administration of dihydrotestosterone (DHT) in a cream, a gel, an aerosolized spray, foam or other manner for delivering dihydrotestosterone (DHT), used alone or in fixed combination with other hair growth medications; including other androgens, bimatoprost, prostamides, prostaglandins, minoxidil or apocrine hair growth factors to promote and enhance hair growth of terminal mustache hair, beard hair, also chest hair, and other male androgen sensitive or dependent hair growth in humans or animals that can be applied to the outer surface of skin areas where a person would hope to increase facial hair growth in the mustache of beard areas, or in the chest area. The embodiment may include one or more lower alcohols, such as ethanol or isopropanol, a penetration enhancing agent such as isopropyl myristate; a thickener; and water. Additionally, the present invention may optionally include salts, emollients, stabilizers, antimicrobials, fragrances, and propellants.

As used herein, the term "lower alcohol," alone or in combination, means a straight-chain or branched-chain alcohol moiety containing one to about six carbon atoms. In one embodiment, the lower alcohol contains one to about 4 carbon atoms, and in another embodiment the lower alcohol contains two to about 3 carbon atoms. Examples of such alcohol moieties include methanol, ethanol, ethanol USP (i.e., 95% v/v), n-propanol, isopropanol, n-butanol, isobutanol, sec-butanol, and tert-butanol. As used herein, the term "ethanol" refers to $C_2H_5OH$. It may be used as dehydrated alcohol USP, alcohol USP, or in any common form including in combination with various amounts of water.

In one embodiment, the present invention is directed to a method for percutaneous administration of dihydrotestosterone (DHT), used alone or in combination, in a hydroalcoholic gel. The gel comprises one or more lower alcohols, such as ethanol or isopropanol; a penetration enhancing agent; a thickener; and water. In one embodiment, the gel comprises an anionic polymer thickening agent precursor neutralized with a hydroxide releasing agent, such as, e.g, sodium hydroxide. Additionally, the present invention may optionally include salts, emollients, stabilizers, antimicrobials, fragrances, and propellants.

EXAMPLES AND SCIENTIFIC STUDY DATA

Example 1

In a single subject clinical trial, a 5% topical lotion of dihydrotestosterone (DHT) was applied to the right upper facial skin area over the upper lip where the mustache hairs normally grow in men. This study was performed in February and March 2008. In this study, a 55 y.o. male who was able to grow a full beard and yet relatively modest mustache hair above the upper lip applied a white 5% dihydrotestosterone (DHT) cream to his right mustache area beginning in mid February 2008.

The 5% dihydrotestosterone (DHT) lotion was applied on a basis of 1 to 3 times a day with a Q-Tip. Over the first four weeks, an assessment by a Board Certified Dermatologist (also Board Certified in Internal Medicine) and a Professor of Medicine and M.D., Ph.D. expert in clinical pharmacology, examined the subject in the clinical trial and both noted a positive difference with more hair growth, more pigmented hairs, longer and more stiff & rigid hairs and more mature hair growth in the mustache area on the right side (treated side) mustache area. This early clinical data suggests that a topical application of a 5% dihydrotestosterone (DHT) compounded cream has a positive effect in growing more mustache hair and more mature, thicker, stiffer, longer, darker and more mature hairs in the mustache area. There were no side effects noted in this study during the four weeks of treatment with 5% topical dihydrotestosterone (DHT). No skin side effects and no systemic side effects were noted. The application of 5% dihydrotestosterone (DHT) cream showed no untoward side effects and was shown to effectively promote desired hair growth in the skin areas of concern.

Bimatoprost

Bimatoprost, a prostamide F 2 alpha analog, is now well documented in the enhancement and promotion of certain specialized hair growth treatments. U.S. Pat. No. 6,262,105 to Johnstone suggests that prostamides and prostaglandin analogs and their derivatives thereof are useful in a method of enhancing hair growth.

Bimatoprost, which is sold by Allergan, Inc. of Irvine, Calif., U.S.A. as Lumigan® ophthalmic solution, for treating glaucoma. Through serendipity, it was found that bimatoprost to be a safe and effective compound to increase the growth, length and pigmentations of eyelash hairs when applied in the FDA approved manner. Allergan, Inc. markets this product as Latisse®.

Bimatoprost is a synthetic prostamide analog with ocular hypotensive activity. Its chemical name is (Z)-7-[(1R,2R,3R,5S)-3,5Dihydroxy-2-[(1E,3S)-3-hydroxy-5-phenyl-1-pentenyl]cyclopentyl]-5-N-ethylheptenamide, and its molecular weight is 415.58. Its molecular formula is $C_{24}H_{37}NO_4$.

Bimatoprost is a powder, which is very soluble in ethyl alcohol and methyl alcohol and slightly soluble in water. In the glaucoma eye drop compound, Lumigan® 0.01% and 0.03%, it is a clear, isotonic, colorless, sterile ophthalmic solution with an osmolality of approximately 290 mOsmol/kg.

In the glaucoma eye drop compound, Lumigan® 0.01% contains Active: bimatoprost 0.1 mg/mL; Preservative: beazalkonium chloride 0.2 mg/mL; Inactives: sodium chloride; sodium phosphate, dibasic; citric acid; and purified water. Sodium hydroxide and/or hydrochloric acid may be added to adjust pH. The pH during its shelf life ranges from 6.8-7.8.

The prostamides are part of a large and continually expanding series of pharmacologically unique neutral lipids. They are COX-2 derived oxidation products of the endocannabinoid/endovanniloid anandamide. Prostamide pharmacology is unique and, as in the case of the endocannabinoids anandamide and 2-arachidonylglycerol, bears little resemblance to that of the corresponding free acids. By virtue of its close relationship to the anti-glaucoma drug bimatoprost, a prostamide F 2 alpha analog, has received the greatest research attention, a prostamide F 2 alpha analog and bimatoprost effects appear independent of prostanoid FP receptor activation, according to a litany of agonist studies. The prostamides are electrochemically neutral biological lipids related to prostaglandins, but with a terminal ethanolamide group. Prostamides appear to work in hair follicles with special prostamide receptors in key parts of the hair follicle.

Over the past ten years, it has been discovered that bimatoprost, can effectively enhance the growth of eyelash hairs, eyebrow hair and even scalp hair. It has been suggested that bimatoprost, may work by having "direct effects" on dermal papilla cells and act via a prostamide receptors located in the dermal papilla cells of the hair follicle. In addition, it has been suggested that bimatoprost, has "indirect effects" on both hair follicle dermal matrix cells and melanocytes located in the hair bulb and in the matrix cells located in the dermal papilla. Both the direct and indirect effects of bimatoprost have been show to lead to the growth of longer, more pigmented and thicker hair in the eyelash, the eyebrow and now the areas of the scalp associated with androgenic alopecia (AA).

On December 2008, the FDA Dermatologic and Ophthalmic Drugs Advisory Committee voted to approve bimatoprost for the cosmetic use of darkening and lengthening eyelashes. The medical term for this is treatment of hypotrichosis; however, the FDA approval was for purely cosmetic purposes. Bimatoprost is a prescription drug in the United States.

In the course of treating patients having glaucoma, treatment may only be appropriate in one eye. Within the course of daily practice it was discovered that a patient who been treated with bimatoprost has lashes that were longer, thicker and fuller in the treated eye than in the non-treated eye. On examination the difference was found to be very striking. The lashes were longer and had a more full dense appearance in the treated eye. The lash appearance on the lids of the treated eye would have appeared quite attractive if it represented a bilateral phenomenon. Because of its asymmetric nature, the long lashes on one side could be construed as disturbing from a cosmetic standpoint. Because of the very unusual appearance a systematic examination of other patients who were taking bimatoprost in only one eye was made. It soon became apparent that this altered appearance was not an isolated finding. Comparison of the lids of patients who were taking bimatoprost in only one eye revealed subtle changes in the lashes and adjacent hairs of the bimatoprost-treated side in several patients. Definite differences could be identified to varying degrees in the lashes and adjacent hairs of all patients who were taking the drug on a unilateral basis for longer than 6 months. These findings were totally unexpected and surprising.

The finding that bimatoprost, which is a prostamide, as explained below. Bimatoprost is not a prostaglandin analog derivative, such as latanoprost, and stimulates hair growth via prostamide receptors located in hair follicle cells.

The changes in the lashes after topical application of bimatoprost were apparent on gross inspection in several patients once attention was focused on the issue. In those with light colored hair and lashes, the differences were only seen easily with the aid of the high magnification and lighting capabilities of the slit lamp biomicroscope. In the course of a glaucoma follow up examination, attention is generally immediately focused on the eye itself. Because of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treated area following administration of bimatoprost were multiple. They included increased length of lashes, increased numbers of lashes along the normal lash line, increased thickness and luster of lashes, increased auxiliary lash-like terminal hair in transitional areas adjacent to areas of normal lash growth, increased lash-like terminal hairs at the medial and lateral canthal area, increased pigmentation of the lashes, increased numbers, increased length, as well as increased luster, and thickness of fine hair on the skin of the adjacent lid, and finally increased perpendicular angulation of lashes and lash-like terminal hairs. The conclusion that hair growth is stimulated by bimatoprost is thus supported not by evidence of a difference in a single parameter but is based on multiple parameters of hair appearance in treated vs. control areas in many subjects. This finding was entirely unexpected and represented a previously unrecognized effect of bimatoprost on stimulation of hair follicles. The modified hairs of the lashes normally turn over slowly and are in their resting phase longer than hair on, for example, the scalp. The ability to cause clear differences in appearance of lashes, the ability to stimulate conversion of vellus or intermediate hair to tea final hairs in transitional areas and the ability to stimulate growth of vellus hair on the skin indicates that bimatoprost is a diversely effective and efficacious agent for the stimulation of hair growth in eyelash hair.

Patients that are treated in or around the eye with compounds of the invention, such as bimatoprost, regularly develop hypertrichosis including altered differentiation, numbers, length, thickness, curvature and pigmentation in the region of treatment.

Some examples of representative bimatoprost analog compounds useful in the practice of the present invention include the compounds shown in Table 1:

Table 1 cyclopentane heptenamide-5-cis-2-(3α-hydroxy-5-phenyl-1-trans-pentenyl)-3,5-dihydroxy, $[1_\alpha, 2_\beta, 3_\alpha, 5_6\alpha]$ cyclopentane N,N-dimethylheptenamide-5-cis-2-(3α-hydroxy-5-phenyl-1-trans-pentenyl)-3,5-dihydroxy, $[1_\alpha, 2_\beta, 3_\alpha, 5_\alpha]$ cyclopentane heptenylamide-5-cis-2-(3α-hydroxy-4-meta-chlorophenoxy-1-trans-pentenyl)-3,5-dihydroxy, $[1_\alpha, 2_\beta, 3_\alpha, 5_\alpha]$ cyclopentane heptenylamide-5-cis-2-(3α-hydroxy-4-trifluoromethylphenoxy-1-trans-pentenyl)-3,5-dihydroxy, $[1_\alpha, 2_\beta, 3_\alpha, 5_\alpha]$ cyclopentane N-isopropyl heptenamide-5-cis-2-(3α-hydroxy-5-phenyl-1-trans-pentenyl)-3,5-dihydroxy, $[1_\alpha, 2_\beta, 3_\alpha, 5_\alpha]$ cyclopentane N-ethyl heptenamide-5-cis-2-(3α-hydroxy-5-phenyl-1-trans-pentenyl)-3,5 dihydroxy, $[1_\alpha, 2_\beta, 3_\alpha, 5_\alpha]$ cyclopentane N-methyl heptenamide-5-cis-2-(3α-hydroxy-5-phenyl-1-trans-pentenyl)-3,5-dihydroxy, $[1_\alpha, 2_\beta, 3_\alpha, 5_\alpha]$ cyclopentane heptenamide-5-cis-2-(3α-hydroxy-4-meta-chlorophenoxy-1-trans-butenyl)-3,5-dihydroxy, $[1_\alpha, 2_\beta, 3_\alpha, 5_\alpha]$ A presently preferred compound for use in the practice of the present invention in a fixed dose combination with dihydrosterone is cyclopentane N-ethyl heptanamide-5-cis-2-(3α-hydroxy-5-phenyl-1-trans-pentenyl)-3,5-dihydroxy, $[1_\alpha, 2_\beta, 3_\alpha, 5_\alpha]$, also known as bimatoprost and sold under the names of Lumigan® and Latisse® by Allergan, Inc., California, USA.

The synthesis of the above compounds described above has been disclosed in U.S. Pat. No. 5,607,978. This patent also shows, particularly in Examples 1, 2, 5 and 7 that these compounds are prostamides, not prostaglandins, in that they do not behave as prostaglandins in art-recognized assays for prostaglandin activity. The invention thus relates to the use of the above compounds, or the prodrugs of these active compounds, for treatment for the stimulation of hair growth. As used herein, hair growth includes hair associated with the mustache, beard, chest hair and other androgen dependent hair in humans and the skin of animals.

In accordance with one aspect of the invention, the compound is mixed with a safe dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth which comprise an effective hair growth stimulating amount of topical dihydrotestosterone, used alone or in a fixed combination, with one or more compounds as defined above and with a dermatologically compatible carrier. Effective amounts of the active compounds may be determined by one of ordinary skill in the art but will vary depending on the compound employed, frequency of application and desired result, and the compound will generally range from about 0.0000001 to about 50%, by weight, of the dermatological composition, preferably, from about 0.001 to about 50%, by weight, of total dermatological composition, more preferably from about 0.1 to about 30%, by weight of the composition.

The present invention finds application in all mammalian species, including both humans and animals. In humans, the compounds of the subject invention can be applied for example, to the face, mustache, beard, and upper lip areas. In animals raised for their pelts, e.g., mink, the compounds can be applied over the entire surface of the body to improve the overall pelt for commercial reasons. There may be benefits for wool production from sheep. The process can also be used for cosmetic reasons in animals, e.g., applied to the skin of dogs and cats having bald patches due to mange or other diseases causing a degree of alopecia.

The pharmaceutical compositions contemplated by this invention include pharmaceutical compositions suited for topical and local action.

The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical formulations in which the compound is applied externally by direct contact with the skin surface to be treated. Conventional pharmaceutical forms for this purpose include liquids, lotions, ointments, liniments, creams, shampoos, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds are applied repeatedly for a sustained period of time topically on the part of the body to be treated. The preferred dosage regimen will generally involve regular, such as daily, administration for a period of treatment of at least one month, more preferably at least three months, and most preferably at least six months.

For topical use, the active compounds can be formulated in aqueous liquids, solutions, lotions, creams, ointments, foams or oils exhibiting physiologically acceptable osmolarity by addition of pharmacologically acceptable buffers and salts. Such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid etc. as additives. Furthermore, particularly aqueous solutions may contain viscosity increasing agents such as polysaccharides, e.g., methylcellulose, mucopolysaccharides, e.g., hyaluronic acid and chondroitin sulfate, or polyalcohol, e.g., polyvinylalcohol. Various slow releasing gels and matrices may also be employed. Depending on the actual formulation and compound to be used, various amounts of the drug and different dose regimens may be employed. Typically, the daily amount of compound for treatment of the eyelid may be about 0.1 ng to about 100 mg per eyelid.

For topical use on the skin, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

Example 2

A study is initiated to systematically evaluate the appearance of lashes and hair around the eyes of patients who are administering bimatoprost in only one eye. The study involves 10 subjects, 5 male, 5 female, average age 70 years, (ranging from 50-94 years). All patients have glaucoma. Each subject is treated daily by the topical application of one drop of bimatoprost at a dosage of 1.5 .mu.g/ml/eye/day (0.03%, by weight, ophthalmic solution, sold under the names Lumigan® and Latisse® by Allergan, Irvine, Calif., U.S.A.) to the region of one eye by instilling the drop onto the surface of the eye. The region of the fellow control eye is not treated with bimatoprost and served as a control.

In the course of treatment with eye drops, there is typically spontaneous tearing, and excess fluid from the drops and associated tears gathers at the lid margins. In the course of wiping the drug containing fluid from the lid margins and adjacent lid, a thin film of the fluid is routinely spread to contact the adjacent skin of the lid area. This widespread exposure of the skin around the lid to the effect of drops is regularly demonstrated in patients who develop a contact dermatitis. Typically the entire area of the upper and lower lid are involved with induration, erythema and edema demonstrating the regular extensive exposure of the ocular adnexa to the influence of topically applied drugs.

The study is limited to subjects who have administered bimatoprost to one eye for more than 3 months. The mean duration of exposure to bimatoprost prior to assessing the parameter of lash growth between the control and study eye is 129 days (range 90-254 days). Observations are made under high magnification at the slit lamp biomicroscope. Documentation of differences between the control and treatment areas is accomplished using a camera specially adapted for use with the slit lamp biomicroscope. The results of the observations are as follows: Length of lashes: Increased length of eyelashes is regularly observed on the side treated with bimatoprost. The difference in length varies from approximately 10% to as much as 30%. Number of lashes: Increased numbers of lashes are observed in the treated eye of each patient. In areas where there are a large number of lashes in the control eye, the increased number of lashes in the bimatoprost-treated eye gave the lashes on the treated side a more thickly matted overall appearance. Auxiliary lash-like hair growth: Several patients have an apparent increase in lash-like hair in transitional areas adjacent to areas of normal lash distribution. These prominent robust appear lash-like hairs appeared to be of comparable length to the actual lashes. These long, thick lash-like hairs were present in the central portion of the lids of several patients in a linear arrangement just above the lash line. Hairs are present at similar locations in the control eyes but are by contrast thinner or more fine in appearance, have less luster and pigment and are more flat against the skin of the lid typical of vellus or intermediate hairs. In several patients, lash-like terminal hairs grow luxuriantly in the medial canthal area in the treated eye. In the corresponding control eye, vellus hairs are seen at the same location. Lash-like hairs are also present in the lateral canthal area of the treated eye but not the control eye in several subjects. Large lashes are not normally present at the lateral canthus and the area is generally free of all but a few occasional very fine lashes or vellus hairs. Increased growth of vellus hair on lids: Fine microscopic vellus hair is present on the skin of the lids and is easily seen with the slit lamp biomicroscope. This vellus hair is typically denser adjacent to and below the lateral portion of the lower lids. While remaining microscopic, vellus hairs are increased in number, appear more robust and are much longer and thicker in treated than in control eyes in the areas below and lateral to the lower lid. Perpendicular angulation of hairs: In areas where there are lash-like hairs above the lash line and in the medial and lateral canthal areas, the hairs are much longer, thicker and heavier. They also leave the surface of the skin at a more acute angle, as though they are stiffer or held in a more erect position by more robust follicles. This greater incline, pitch, rise or perpendicular angulation from the skin surface gives the appearance of greater density of the hairs.

The foregoing observations clearly establish that bimatoprost can be used to increase the growth of eyelash hair in humans. This conclusion is based on the regular and consistent finding of manifestations of increased hair growth in treated vs. control areas in human subjects. The conclusion that the drug bimatoprost is capable of inducing increased robust growth of eyelash hair is based not on a single parameter, i.e., length, but is based on multiple lines of evidence as described in the results. Detailed examination and description of differences in hair is greatly facilitated by the ability to examine the hairs at high magnification under stable conditions of fixed focal length and subject position utilizing the capabilities of the slitlamp biomicroscope.

Example 3

A topical cream is prepared as follows: Tegacid and spermaceti are melted together at a temperature of 70-80° C. Methylparaben is dissolved in about 500 gm of water and propylene glycol, polysorbate 80, and bimatoprost are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example 4

A topical cream is prepared as follows: Tegacid and spermaceti are melted together at a temperature of 70-80° C. Methylparaben is dissolved in water and propylene glycol, polysorbate 80, and bimatoprost are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

The composition is applied to bald human scalp once daily to stimulate the growth of hair.

Example 5

An ointment containing 2% by weight bimatoprost is prepared as follows: White petrolatum and wool fat are melted, strained and liquid petrolatum is added thereto. The bimatoprost, zinc oxide, and calamine are added to the remaining liquid petrolatum and the mixture milled until the powders are finely divided and uniformly dispersed. The mixture is stirred into the white petrolatum, melted and cooled with stirring until the ointment congeals. The foregoing ointment can be applied topically to mammalian skin for increased rate of hair growth, and can be prepared by omitting the zinc oxide and calamine.

Example 6

A dermatological ophthalmic ointment containing 10% by weight bimatoprost is prepared by adding the active compound to light liquid petrolatum. White petrolatum is melted together with wool fat, strained, and the temperature adjusted to 45-50° C. The liquid petrolatum slurry is added and the ointment stirred until congealed. Suitably the ointment is packaged in 30 gm tubes. The foregoing ointment can be applied to the eyelid to enhance the growth of eyelashes. Similarly the composition can be applied to the brow for eyebrow growth.

Example 7

An aqueous solution containing 5%, by weight, bimatoprost is prepared as follows. Bimatoprost is dissolved in water and the resulting solution is sterilized by filtration. The solution is aseptically filled into sterile containers. The composition so prepared can be used in the topical treatment of baldness by application to the scalp daily.

Example 8

A sample of bimatoprost is dissolved in the vehicle of N-methylpyrrolidone and propylene glycol. The composition can be used for application to dogs or cats having hair loss due to mange or alopecia of other causes.

Example 9

An aerosol containing approximately 0.1% by weight bimatoprost is prepared by dissolving the bimatoprost in absolute alcohol. The resulting solution filtered to remove particles and lint. This solution is chilled to about minus 30° C. To the solution is added a chilled mixture of dichlorodifluoromethane and dichlorotetrafluoroethane.

Thirteen ml plastic-coated amber bottles are cold filled with 11.5 gm each of the resulting solution and capped. The composition can be sprayed on the scalp daily to stimulate the growth of hair.

Example 10

A powder of the compound bimatoprost is prepared by mixing in dry form with talcum powder at a weight/weight ratio of 1:10. The powdered mixture is dusted on the fur of minks or other commercially valuable fur bearing animals and show animals for increased rate of hair growth.

Example 11

Following the procedure of he preceding examples, compositions are similarly prepared substituting an equimolar amount of a compound of Table 1 for the bimatoprost disclosed in the preceding Examples. Similar results are obtained. While the preferred embodiment of the invention has been illustrated and described, it will be appreciated that various changes can be made therein without departing from the spirit and scope of the invention.

Minoxidil

Use of the compound minoxidil is now well documented in the enhancement and promotion of certain specialized hair growth treatments. Minoxidil has been show to slow down rate and androgenic alopecia and in some cases help regrow new hair on the scalp. Generally, minoxidil has been only able to grow vellus hair.

Minoxidil is an antihypertensive vasodilator medication. It also slows or stops hair loss and promotes hair regrowth. Now off-patent, it is available over-the-counter for the treatment of androgenic alopecia. Minoxidil must be used indefinitely for continued support of existing hair follicles and the maintenance of any experienced hair regrowth. It is marketed under many trade names.

It has a formula $C_9H_{15}N_5O$. It has a molecular weight of 209.251 g/mol

Originally, minoxidil was used exclusively as an oral drug (with the trade name Loniten®) to treat high blood pressure. However, it was discovered to have an interesting side effect: hair growth. Minoxidil may cause increased growth or darkening of fine body hairs, or in some cases, significant hair growth. When the medication is discontinued, the hair loss will return to normal rate within 30 to 60 days. Upjohn Corporation produced a topical solution that contained 2% minoxidil to be used to treat baldness and hair loss, under the brand name Rogaine® in the United States and Canada, and Regaine® in Europe and the Asia-Pacific. The patent on minoxidil expired Feb. 11, 1996. Treatments usually include a 5% concentration solution that is designed for men, and a 2% concentration solution for women. While the drug is available in the United Kingdom, it cannot be prescribed on the NHS, so patients must either buy it over-the-counter or have a private prescription for it.

The mechanism by which minoxidil promotes hair growth is not fully understood. Minoxidil contains the nitric oxide chemical moiety and may act as a nitric oxide agonist. Similarly, minoxidil is a potassium channel opener, causing hyperpolarization of cell membranes. Minoxidil is less effective when there is a large area of hair loss. In addition, its effectiveness has largely been demonstrated in younger men who have experienced hair loss for less than 5 years. Minoxidil use is indicated for central (vertex) hair loss only. Minoxidil is also a vasodilator, Hypothetically, by widening blood vessels and opening potassium channels, it allows more oxygen, blood, and nutrients to the follicle. This may cause follicles in the telogen phase to shed, which are then replaced by thicker hairs in a new anagen phase.

Minoxidil when taken orally has been known to induce hair growth in extensive areas of the back, trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed.

An example of such a drug is diphenylhydantoin which is an anticonvulsant drug widely used to control epileptic seizures. Hypotrichosis is frequently observed in epileptic children some two or three months after starting the drug and first becomes noticeable on the extensor aspects of the limbs and later on the trunk and face. (The same pattern of hypotrichosis is sometimes caused by injury to the head.) As for the hair, it is often shed when the drug is discontinued but may, in some circumstances, remain.

Streptomycin is another drug that has been found to produce hypotrichosis, in much the same way as diphenylhydantoin, when administered to children suffering from tuberculous meningitis. About the same effects were observed and the onset and reversal of the hypotrichosis in relation to the period of treatment with the antibiotic leave little question but that it was the causative agent.

In addition to the foregoing, it has been reported in U.S. Pat. Nos. 4,139,619 and 4,968,812, that the compound minoxidil is useful for the treatment of male pattern baldness. That compound, among others, has proven to have considerable therapeutic value in the treatment of severe hypertension. It is a so-called anti-hypertensive "vasodilator" which, as the name implies, functions to dilate the peripheral vascular system. First introduced as an oral drug to treat high blood pressure, topical solutions and foam products were introduced to prevent or treat hair loss. Dermatologists and others have recognized that prolonged vasodilatation of certain areas of the human body other than the scalp sometimes result in increased hair growth even in the absence of any vasodilating therapeutic agent. For instance, increased hair growth around surgical scars is not uncommon. Similarly, arteriovenous fistula have been known to result in increased vascularity accompanied by enhanced hair growth. Externally-induced vasodilation of the skin, such as, for example, by repeated biting of the limbs by the mentally retarded and localized stimulation of the shoulders by water carries has been known to bring on hypotrichosis in the affected areas. Be that as it may, similar techniques such as continued periodic massage of the scalp have been found to be totally ineffective as a means for restoring lost hair growth to the scalp. Scar tissue on the scalp inhibits rather than promotes hair growth.

An alternative embodiment of the present invention provides pharmaceutical fixed compositions for topical application to enhance hair growth comprising an effective amount dihydrotestosterone with cyclopentane N-ethyl heptanamide-5-cis-2-(3α-hydroxy-5-phenyl-1-trans-pentenyl)-3,5-dihydroxy, $[1_\alpha, 2_\beta, 3_\alpha, 5_\alpha]$, also known as bimatoprost, along with minoxidil.

Another aspect of the invention provides methods for stimulating the rate of hair growth and for stimulating the conversion of vellus hair or intermediate hair to growth as terminal hair in a human or non-human by administering to the skin an effective amount of dihydrotestosterone, bimatoprost and minoxidil, wherein the additional combination of bimatoprost and minoxidil obtains the above results in a synergistic manner as compared to bimatoprost and minoxidil, alone.

The terms "effective amount", "therapeutically effective amount" or "pharmaceutically effective amount" as used herein refers to that amount of the therapeutic agent sufficient to ameliorate one or more aspects of the disorder. The result can be reduction and/or alleviation of the signs, symptoms, or causes of a disease, or any other desired alteration of a biological system. For example, an "effective amount" for therapeutic uses is the amount of the composition comprising an agent as set forth herein required to provide a clinically significant decrease in an ophthalmic disease. For example, for the given aspect (e.g., length of incidence), a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease.

For example, a therapeutically effective amount can have at least a 1.2-fold, 1.5-fold, 2-fold, 5-fold, or more effect over a control. An appropriate "effective" amount in any individual case may be determined using techniques, such as a dose escalation study.

Other Discussion

Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "disease" refers to any deviation from the normal health of a mammal and includes a state when disease symptoms are present, as well as conditions in which a deviation (e.g., infection, gene mutation, genetic defect, etc.) has occurred, but symptoms are not yet manifested. According to the present invention, the methods disclosed herein are suitable for use in a patient that is a member of the Vertebrate class, Mammalia, including, without limitation, primates, livestock and domestic pets (e.g., a companion animal). Typically, a patient will be a human patient.

As used herein, "topical application," "topical administration," acid "topically administering" are used interchangeably herein and include the administration of a composition to the upper and/or lower eyelid margin, eyebrow region, scalp or face. Topical application or administering may result in the delivery of an active agent to the eye or skin or a localized region of the body.

"Topical formulation" and "topical pharmaceutical composition" are used interchangeably herein and include a formulation that is suitable for topical application to the face, upper lip or chest areas. Specific topical formulations can be used for topical, local, regional, or transdermal application of substances.

As used herein, the terms "application," "apply," and "applying" used in reference to a topical composition product or method of using a composition or a product, refer to any mariner of administering a topical composition or a product to the eye, the mucosal or dermal area proximal to the eye of a patient which, in medical or cosmetology practice, delivers the composition or the product to patient's eye, the mucosal or dermal area proximal to the eye. Smearing, rubbing, spreading, spraying a topical composition, with or without the aid of suitable devices, on a patient's skin are all included within the scope of the term "application," as used herein. The term "topical" or "topically" in reference to administration or application of a composition or a product refers to epicutaneous administration or application, or administration onto skin. The term-"topically active agent" as used herein refers to a compound that is effective in a treatment of a skin condition when administered topically. It is to be understood that topically active agent can have a local or a systemic effect, or both, when administered topically. The term "topical," when used in reference to a composition or a product refers to a composition or a product formulated for topical application.

The abbreviations used herein have their conventional meaning within the chemical, biological or pharmaceutical arts.

The terms "about" and "approximately equal" are used herein to modify a numerical value and indicate a defined range around that value. If "X" were the value, "about X" or "approximately equal to X" would generally indicate a value from 0.90X to 1.10X. Any reference to "about X" minimally indicates at least the values X, 0.90X, 0.91X, 0.92X, 0.93X, 0.94X, 0.95X, 0.96X, 0.97X., 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%." "About" may also include variations in the amount that a regulatory body such as the FDA or EMEA would view as bioequivalent to the claimed amount.

As used herein, the phrase "pharmaceutically acceptable salts" refers to salts of the active compound(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, under ylenic acid, naturally and synthetically derived amino acids. Non-limiting examples of base salts include ammonium salts; alkali metal salts, such as sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others.

"Prodrugs" refer to compounds which are a precursor of a compound and that is converted into its active form, for example, in the body by normal metabolic processes. Alopecia (baldness) a deficiency of either normal or abnormal hair is primarily a cosmetic problem in humans. It is a deficiency of terminal hair, the broad diameter, colored hair that is readily seen. However, in the so-called bald person although there is a noticeable absence of terminal hair, the bald scalp skin may contain vellus hair which is a fine colorless hair which may require microscopic examination to determine its presence. This vellus hair is a precursor to terminal hair. In some case of scalp alopecia, hair follicles have been destroyed by the long term impact of 5 alpha reductase and the impact of dihydrotestosterone, and other factors.

Drug synergism occurs when drugs can interact in ways that enhance, magnify or synergistically amplify one or more desired effects, or side effects, of those drugs. Negative effects of synergy are a form of contraindication such as when more than one depressant drug is used that affects the central nervous system (CNS), an example being alcohol and Valium. The combination can cause a greater reaction than simply the sum of the individual effects of each drug if they were used separately. In this particular case, the most serious consequence of drug synergy is exaggerated respiratory depression, which can be fatal if left untreated.

Synergism has also been noted in describing how complex systems operate. For example, biological systems may react in a non-linear way to perturbations, so that the outcome may be greater than the sum of the individual component alterations.

In describing the present invention, synergism means that the combination of the two active drugs, utilized in the methods and compositions of the invention achieves a result, e.g. stimulating the growth of hair such as eyelashes, in a mammal, e.g. a human, that is greater than the result achieved when the active drugs are utilized, alone, under the same conditions. Thus, to determine the combinations that are within the scope of the present invention, one may simply compare the result achieved by the combination of the two drugs with the result achieved with each of the individual drugs, alone.

In accordance with the invention as described herein, there is provided a method for enhancing hair growth in a mammal in need thereof which comprises administering to the mammal a synergistically effective amount of dihydrotestosterone, testosterone, bimatoprost other prostamides or minoxidil. Thus, in accordance with the present invention, synergistically effective amounts of testosterone and/or, bimatoprost and/or minoxidil, other prostamides and/or are used with dihydrotestosterone to stimulate the conversion of vellus hair to growth as terminal hair as well as increase the rate of growth of terminal hair in the mustache, beard, chest and other androgenic dependent hair growth areas.

In said method of this invention, the concentration of added bimatoprost and/or minoxidil are administered as a composition comprising from 0.0000001% to 10% bimatoprost and from 0.001% to 10% minoxidil, by weight.

Some concentrations of minoxidil include from about 0.001 to about 5 to about 10% w/w, from about 0.005 to about 5, from about 0.01 to about 5, from about 0.05 to about 5, from about 0.1 to about 5, from about 0.5 to about 5, from about 1 to about 5, from about 1.5 to about 5, from about 2 to about 5, from about 2.5 to about 5, from about 3 to about 5, from about 3.5 to about 5, from about 4 to about 5, from about 4.5, from about 0.001 to about 4.5, from about 0.005 to about 4.5, from about 0.01 to about 4.5, from about 0.05 to about 4.5, from about 0.1 to about 4.5, from about 0.5 to about 4.5, from about 1 to about 4.5, from about 1.5 to about 4.5, from about 2 to about 4.5, from about 2.5 to about 4.5, from about 3 to about 4.5, from about 3.5 to about 4.5, from about 4 to about 4.5, from about 0.001 to about 4, from about 0.005 to about 4, from about 0.01 to about 4, from about 0.05 to about 4, from about 0.1 to about 4, from about 0.5 to about 4, from about 1 to about 4, from about 1.5 to about 4, from about 2 to about 4, from about 2.5 to about 4, from about 3 to about 4, from about 3.5 to about 4, from about 0.001 to about 3.5, from about 0.005 to about 3.5, from about 0.01 to about 3.5, from about 0.05 to about 3.5, from about 0.1 to about 3.5, from about 0.5 to about 3.5, from about 1 to about 3.5, from about about 3.5, from about 2 to about 3.5, from about 2.5 to about 3.5, from about 3 to about 3.5, from about 0.001 to about 3 from about 0.005 to about 3, from about 0.01 to about 3, from about 0.05 to about 3, from about 0.1 to about 3, from about 0.5 to about 3, from about 1 to about 3, from about 1.5 to about 3, from about 2 to about 3, from about 2.5 to about 3, from about 0.001 to about 2.5, from about 0.005 to about 2.5, from about 0.01 to about 2.5, from about 0.05 to about 2.5, from about 0.1 to about 2.5, from about 0.5 to about 2.5, from about 1 to about 2.5, from about 1.5 to about 2.5, from about 2 to about 2.5, from about 0.001 to about 2 from about 0.005 to about 2, from about 0.01 to about 2, from about 0.05 to about 2, from about 0.1 to about 2, from about 0.5 to about 2, from about 1 to about 2, from about 1.5 to about 2, from about 0.001 to about 1.5, from about 0.005 to about 1.5, from about 0.01 to about 1.5, from about 0.05 to about 1.5, from about 0.1 to about 1.5, from about 0.5 to about 1.5, from about 1 to about 1.5, from about 0.001 to about 1, from about 0.005 to about 1, from about 0.01 to about 1, from about 0.05 to about 1, from about 0.1 to about 1, from about 0.5 to about 1, from about 0.001 to about 0.5, from about 0.005 to about 0.5, from about 0.01 to about 0.5, from about 0.05 to about 0.5, from about 0.1 to about 0.5, from about 0.001 to about 0.1, from about 0.005 to about 0.1, from about 0.01 to about 0.1, from about 0.05 to about 0.1, from about 0.001 to about 0.05, from about 0.005 to about 0.05, from about 0.01 to about 0.05, or from about 0.001 to about 0.005% (w/w). In some embodiments, the minoxidil is present at about 0.001, 0.005, 0.01, 0.05, 0.1, 0.5, 1, 1.5, 2, 2.5, 3, 3.5, 4, 4.5, or 5%).

Minoxidil may also be present in 5.5% to about 10% w/w, from about 6% w/w to about 10% w/w, from about 6.5% w/w to about 10% w/w, from about 7% w/w to about 10% w/w, from about 7.5% w/w to about 10% from about 8% w/w to about 10% w/w, from about 8.5% w/w to about 10% w/w, from about 9% w/w to about 10% w/w, from about 9.5% w/w to about 10% w/w, from about 5% w/w to about 9.5% w/w, 5.5% w/w to about 9.5% w/w, from about 6% w/w to about 9.5% w/w, from about 6.5% w/w to about 9.5% w/w, from about 7% w/w to about 9.5% w/w, from about 7.5% w/w to about 9.5% w/w, from about 8% w/w to about 9.5% w/w, from about 8.5% w/w to about 9.5% w/w, from about 9% to about 9.5% w/w, from about 5% w/w to about 9% w/w, 5.5% w/w to about 9% w/w, from about 6% w/w to about 9% w/w, from about 6.5% w/w to about 9% w/w, from about 7% w/w to about 9% w/w, from about 7.5% w/w to about 9% w/w, from about 8% w/w to about 9% w/w, from about 8.5% w/w to about 9% w/w, from about 5% w/w to about 8.5% w/w, 5.5% w/w to about 8.5% w/w, from about 6% w/w to about 8.5% w/w, from about 6.5% w/w to about 8.5% w/w, from about 7% w/w to about 8.5% w/w, from about 7.5% w/w to about 8.5% w/w, from about 8% w/w to about 8.5% w/w, from about 5% w/w to about 8% w/w, 5.5% w/w to about 8% w/w, from about 6% w/w to about 8% w/w, from about 6.5% w/w to about 8% w/w, from about 7% w/w to about 8% w/w, from about 7.5% w/w to about 8% w/w, from about 5% w/w to about 7.5% w/w, 5.5% w/w to about 7.5% w/w, from about 6% w/w to about 7.5% w/w, from about 6.5% w/w to about 7.5% w/w, from about 7% w/w to about 7.5% w/w, from about 5% w/w to about 7% w/w, 5.5% w/w to about 7% w/w, from about 6% w/w to about 7% w/w, from about 6.5% w/w to about 7% w/w, from about 5% w/w to about 6.5% w/w, 5.5% w/w to about 6.5% w/w, or from about 6% w/w to about 6.5% w/w. In some embodiments, minoxidil is present at about 5, 5.5, 6, 6.5, 7, 7.5, 8, 8.5, 9, 9.5 or 10% (w/w).

Formulating Fixed Dose Combinations

Bimatoprost, as recited above and here presented in greater detail, may be present at 0.1 or 0.3% w/v. Other concentrations that bimatoprost may be present are about 0.005 to about 5, from about 0.01 to about 5, from about 0.05 to about 5, from about 0.1 to about 5, from about 0.5 to about 5, from about 1 to about 5, from about 1.5 to about 5, from about 2 to about 5, from about 2.5 to about 5, from about 3 to about 5, from about 3.5 to about 5, from about 4 to about 5, from about 4.5, from about 0.001 to about 4.5, from about 0.005 to about 4.5, from about 0.01 to about 4.5, from about 0.05 to about 4.5, from about 0.1 to about 4.5, from about 0.5 to about 4.5, from about 1 to about 4.5, from about 1.5 to about 4.5, from about 2 to about 4.5, from about 2.5 to about 4.5, from about 3 to about 4.5, from about 3.5 to about 4.5, from about 4 to about 4.5, from about 0.001 to about 4, from about 0.005 to about 4, from about 0.01 to about 4, from about 0.05 to about 4, from about 0.1 to about 4, from about 0.5 to about 4, from about 1 to about 4, from about 1.5 to about 4, from about 2 to about 4, from about 2.5 to about 4, from about 3 to about 4, from about 3.5 to about 4, from about 0.001 to about 3.5, from about 0.005 to about 3.5, from about 0.01 to about 3.5, from about 0.05 to about 3.5, from about 0.1 to about 3.5, from about 0.5 to about 3.5, from about 1 to about 3.5, from about 1.5 to about 3.5, from about 2 to about 3.5, from about 2.5 to about 3.5, from about 3 to about 3.5, from about 0.001 to about 3, from about 0.005 to about 3, from about 0.01 to about 3, from about 0.05 to about 3, from about 0.1 to about 3, from about 0.5 to about 3, from about 1 to about 3, from about 1.5 to about 3, from about 2 to about 3, from about 2.5 to about 3, from about 0.001 to about 2.5, from about 0.005 to about 2.5, from about 0.01 to about 2.5, from about 0.05 to about 2.5, from about 0.1 to about 2.5, from about 0.5 to about 2.5, from about 1 to about 2.5, from about 1.5 to about 2.5, from about 2 to about 2.5, from about 0.001 to about 2, from about 0.005 to about 2, from about 0.01 to about 2, from about 0.05 to about 2, from about 0.1 to about 2, from about 0.5 to about 2, from about 1 to about 2, from about 1.5 to about 2, from about 0.001 to about 1.5, from about 0.005 to about 1.5, from about 0.01 to about 1.5, from about 0.05 to about 1.5, from about 0.1 to about 1.5, from about 0.5 to about 1.5, from about 1 to about 1.5, from about 0.001 to about 1, from about 0.005 to about 1, from about 0.01 to about 1, from about 0.05 to about 1, from about 0.1 to about 1, from about 0.5 to about 1, from about 0.001 to about 0.5, from about 0.005 to about 0.5, from about 0.01 to about 0.5, from about 0.05 to about 0.5, from about 0.1 to about 0.5, from about 0.001 to about 0.1, from about 0.005 to about 0.1, from about 0.01 to about 0.1, from about 0.05 to about 0.1, from about 0.001 to about 0.05, from about 0.005 to about 0.05, from about 0.01 to about 0.05, or from about 0.001 to about 0.005% (w/w). In some embodiments, bimatoprost is present at about 0.001, 0.005, 0.01, 0.05, 0.1, 0.5, 1, 1.5, 2, 2.5, 3, 3.5, 4, 4.5, or 5% (w/w).

In a further aspect of the invention, there is provided a method for alleviating a condition characterized by inadequate or lack of hair, in or on a warm-blooded animal, which comprises topically or otherwise locally administering to said animal an effective amount of a pharmaceutical composition comprising: (1) a combination of dihydrotestosterone, and/or other androgens, and/or bimatoprost, an/or other prostamides, and/or prostaglandins, and/or minoxidil in a synergistically effective amount and (2) a non-toxic, pharmaceutically acceptable carrier therefore suitable for topical or other local application.

In accordance with one aspect of the invention, the drugs dihydrotestosterone, testosterone, bimatoprost and/or minoxidil, are mixed with a dermatologically compatible vehicle or carrier. The vehicle which may be employed for preparing compositions of this invention may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

The invention is also related to dermatological compositions for topical treatment for the stimulation of hair growth, which comprise an effective hair growth stimulating amount of dihydrotestosterone, testosterone, bimatoprost and/or minoxidil and a dermatologically compatible carrier. Effective amounts of the active compounds may be determined by one of ordinary skill in the art but will vary depending on the frequency of application and desired result, and bimatoprost will range from about 0.0000001 to about 10%, by weight, of the dermatological composition, preferably from about 0.001 to about 10%, by weight, of total dermatological composition, more preferably from about 0.03 to about 5%, by weight, of the composition and minoxidil will range from about 0.001 to about 10%, by weight, of the dermatological composition, preferably from about 0.01 to about 10%, by weight, of the composition.

The following specific combinations of bimatoprost and minoxidil in a dermatological compatible carrier are contemplated as being effective when combined with dihydrotestosterone to achieve the object of this invention, i.e. enhancing hair growth in a mammal in need thereof by administering to the mammal an effective amount of bimatoprost and minoxidil: Certain of these combinations may be synergistic. Other specific combinations within the scope of the concentrations, given below, i.e. 0.1 to 10 percent minoxidil and 0.01 and 0.5 bimatoprost are also contemplated as useful in the method of the present invention.

TABLE I

| Bimatoprost Weight percent w/w | Minoxidil Weight percent w/w |
| --- | --- |
| 0.01 | any one of 0.1, 1.0, 2.0, 3.0, 4.0, 5.0, 6.0, 7.0, 8.0, 9.0 and 10.0; |
| 0.02 | and any one of 0.1, 1.0, 2.0, 3.0, 4.0, 5.0, 6.0, 7.0, 8.0, 9.0 and 10.0; |
| 0.03 | and any one of 0.1, 1.0, 2.0, 3.0, 4.0, 5.0, 6.0, 7.0, 8.0, 9.0 and 10.0; |
| 0.04 | and any one of 0.1, 1.0, 2.0, 3.0, 4.0, 5.0, 6.0, 7.0, 8.0, 9.0 and 10.0; |
| 0.05 | and any one of 0.1, 1.0, 2.0, 3.0, 4.0, 5.0, 6.0, 7.0, 8.0, 9.0 and 10.0; |
| 0.1 | and any one of 0.1, 1.0, 2.0, 3.0, 4.0, 5.0, 6.0, 7.0, 8.0, 9.0 and 10.0; |
| 0.2 | and any one of 0.1, 1.0, 2.0, 3.0, 4.0, 5.0, 6.0, 7.0, 8.0, 9.0 and 10.0; |
| 0.3 | and any one of 0.1, 1.0, 2.0, 3.0, 4.0, 5.0, 6.0, 7.0, 8.0, 9.0 and 10.0; |
| 0.5 | and any one of 0.1, 1.0, 2.0, 3.0, 4.0, 5.0, 6.0, 7.0, 8.0, 9.0 and 10.0 and |
| 1.0 | and any one of 0.1, 1.0, 2.0, 3.0, 4.0, 5.0, 6.0, 7.0, 8.0, 9.0 and 10.0. |

In particular, the following specific combinations of bimatoprost and minoxidil in a dermatologically compatible carrier are contemplated as being effective to achieve the object of this invention, i.e. enhancing hair growth in a human and non human mammal in need thereof by administering to the mammal an effective amount of bimatoprost and minoxidil:

TABLE 2

| Bimatoprost Weight percent w/w | Minoxidil Weight percent w/w |
|---|---|
| 0.01 | 0.1 |
| 0.01 | 1.0 |
| 0.02 | 2.0 |
| 0.03 | 3.0 |
| 0.04 | 4.0 |
| 0.05 | 5.0 |
| 0.06 | 6.0 |
| 0.07 | 7.0 |
| 0.1 | 8.0 |
| 0.3 | 9.0 |
| 0.5 | 10.0 |

Example 12

A study is initiated to systematically evaluate the appearance of lashes and hair around the eyes of patients by administering a topical composition comprising 0.03% bimatoprost and 5% minoxidil, by weight, in the area of the eyelid of only one eye. The study involves 10 subjects, 5 male, 5 female, average age 70 years, (ranging from 50-94 years). Each subject is treated daily by the topical application of one drop of bimatoprost at a dosage of 1.5 μg/ml/eye/day to the region of one eye by instilling the drop onto the surface of the eyelid. The region of the fellow control eye is not treated and served as a control.

Observations are made under high magnification at the slit lamp biomicroscope.

Documentation of differences between the control and treatment areas is accomplished using a camera specially adapted for use with the slit lamp biomicroscope.

The results of the observations will be as follows:

Length of lashes: increased length of eyelashes is regularly observed on the side treated with bimatoprost. The difference in length varies from approximately 10% to as much as 30%.

Number of lashes: Increased numbers of lashes are observed in the treated eye of each patient. In areas where there are a large number of lashes in the control eye, the increased number of lashes in the treated eye gave the lashes on the treated side a more thickly matted overall appearance.

Auxiliary lash-like hair growth: Several patients have an apparent increase in lash-like hair in transitional areas adjacent to areas of normal lash distribution. These prominent robust appear lash-like hairs appeared to be of comparable length to the actual lashes. These long, thick lash-like hairs were present in the central portion of the lids of several patients in a linear arrangement just above the lash line. Hairs are present at similar locations in the control eyes but are by contrast thinner or finer in appearance, have less luster and pigment and are more flat against the skin of the lid typical of vellus or intermediate hairs. In several patients, lash-like terminal hairs grow luxuriantly in the medial canthal area in the treated eye. In the corresponding control eye, vellus hairs are seen at the same location. Lash-like hairs are also present in the lateral canthal area of the treated eye but not the control eye in several subjects. Large lashes are not normally present at the lateral canthus and the area is generally free of all but a few occasional very fine lashes or vellus hairs.

Increased growth of vellus hair on lids: Fine microscopic vellus hair is present on the skin of the lids and is easily seen with the slit lamp biomicroscope. This vellus hair is typically denser adjacent to and below the lateral portion of the lower lids. While remaining microscopic, vellus hairs are increased in number appear more robust and are much longer and thicker in treated than in control eyes in the areas below and lateral to the lower lid.

Perpendicular angulation of hairs: In areas where there are lash-like hairs above the lash line and in the medial and lateral canthal areas, the hairs are much longer, thicker and heavier. They also leave the surface of the skin at a more acute angle, as though they are stiffer or held in a more erect position by more robust follicles. This greater incline, pitch, rise or perpendicular angulation from the skin surface gives the appearance of greater density of the hairs.

The foregoing observations will clearly establish that above composition can be used to increase the growth of hair in man. This conclusion is based on the regular and consistent finding of manifestations of increased hair growth in treated vs. control areas in human subjects. The conclusion that the composition of this invention is capable of inducing increased robust growth of hair is based not on a single parameter, i.e., length, but is based on multiple lines of evidence as described in the results. Detailed examination and description of multiple parameters of differences in hair is greatly facilitated by the ability to examine the hairs at high magnification under stable conditions of fixed focal length and subject position utilizing the capabilities of the slitlamp biomicroscope.

Example 13

A topical cream is prepared as follows: Tegacid and spermaceti are melted together at a temperature of 70-80° C. Methylparaben is dissolved in about 500 gm of water and propylene glycol, polysorbate 80, and bimatoprost and minoxidil are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

Example 14

A topical cream is prepared as follows: Tegacid and spermaceti are melted together at a temperature of 70-80° C. Methylparaben is dissolved in water and propylene glycol, polysorbate 80, dihydrotestosterone, 0.5 to 20%, and bimatoprost, 0.001% to 0.1%, is added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed. The composition is applied to bald human skin once daily to stimulate the growth of hair.

Example 15

A topical cream is prepared as follows: Tegacid and spermaceti are melted together at a temperature of 70-80° C. Methylparaben is dissolved in water and propylene glycol, polysorbate 80, dihydrotestosterone, 0.5 to 20%, bimatoprost, 0.001% to 0.1%, and/or minoxidil 2% to 5%, are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed. The composition is applied to bald human skin once daily to stimulate the growth of hair.

Example 16

A topical cream is prepared as follows: Tegacid and spermaceti are melted together at a temperature of 70-80° C. Methylparaben is dissolved in water and propylene glycol, polysorbate 80, dihydrotestosterone, 0.5 to 20%, bimatoprost, 0.001% to 0.1%, and/or minoxidil 2% to 5%, and/or testosterone 1% to 20%, are added in turn, maintaining a temperature of 75-80° C. The methylparaben mixture is added slowly to the Tegacid and spermaceti melt, with constant stirring. The addition is continued for at least 30 minutes with additional stirring until the temperature has dropped to 40-45° C. Finally, sufficient water is added to bring the final weight to 1000 gm and the preparation stirred to maintain homogeneity until cooled and congealed.

The composition is applied to bald human skin once daily to stimulate the growth of hair.

Example 17

An ointment containing bimatoprost and minoxidil is prepared as follows: White petrolatum and wool fat are melted, strained and liquid petrolatum is added thereto. The bimatoprost, minoxidil, zinc oxide, and calamine are added to the remaining liquid petrolatum and the mixture milled until the powders are finely divided and uniformly dispersed. The mixture is stirred into the white petrolatum, melted and cooled with stirring until the ointment congeals. The foregoing ointment can be applied topically to mammalian skin for increased rate of hair growth, and can be prepared by omitting the zinc oxide and calamine.

Example 18

A dermatological ophthalmic ointment containing bimatoprost and minoxidil is prepared by adding the active compounds to light liquid petrolatum. White petrolatum is melted together with wool fat, strained, and the temperature adjusted to 45-50° C. The liquid petrolatum slurry is added and the ointment stirred until congealed. Suitably the ointment is packaged in 30 gm tubes. The foregoing ointment can be applied to the eyelid to enhance the growth of eyelashes. Similarly the composition can be applied to the brow for eyebrow growth.

Example 19

An aqueous solution containing bimatoprost and minoxidil is prepared as follows. Bimatoprost and minoxidil are dissolved in water and the resulting solution is sterilized by filtration. The solution is aseptically filled into sterile containers.

The composition so prepared can be used in the topical treatment of baldness by application to the scalp daily.

Example 20

Bimatoprost and minoxidil are dissolved in a vehicle of N-methylpyrrolidone and propylene glycol. The composition can be used for application to dogs or cats having hair loss due to mange or alopecia of other causes.

Example 21

An aerosol containing approximately 0.03% by weight bimatoprost and 5%, by weight minoxidil is prepared by dissolving the bimatoprost and minoxidil in absolute alcohol. The resulting solution filtered to remove particles and lint. This solution is chilled to about minus 30° C. To the solution is added a chilled mixture of dichlorodifluoromethane and dichlorotetrafluoroethane. Thirteen ml plastic-coated amber bottles are cold filled with 11.5 gm each of the resulting solution and capped. The composition can be sprayed on the scalp daily to stimulate the growth of hair.

Example 22

A foamable liquid composition containing approximately 0.03% by weight bimatoprost and 5%, by weight minoxidil is prepared by dissolving the bimatoprost and minoxidil in an alcohol-containing solvent. Said foamable liquid composition further includes a solvent system, a surfactant and a foam stabilizer. The solvent system, includes water, an alcohol and, optionally, an acid and a water soluble solvent. This composition is prepared by methods known in the art. A method of delivering a foam product according to the present invention comprises the following steps: providing a foamable liquid composition comprising 5 percent, by weight, minoxidil and 0.03 percent, by weight, bimatoprost or a pharmaceutically acceptable salt of either or both of minoxidil or bimatoprost, in an amount or amounts sufficient to provide: 5 percent, by weight, minoxidil, and 0.03 percent, by weight, bimatoprost in a container adapted for dispensing the foamable liquid composition as a foam and dispensing the foamable liquid composition as a foam from said container onto the skin of a patient. Alternatively, minoxidil may be used in an amount of from 0.5 to 10 percent and preferably in an amount of from 2 to 5 percent, by weight, relative to the total weight of the foamable liquid composition. Bimatoprost may be used in an amount of from 0.01 to 3 percent and more preferably in an amount of from 0.03 to 1 percent, by weight, relative to the total weight of the liquid composition. The solvent system is an aqueous-alcoholic medium, which enables solubilization of minoxidil and bimatoprost. In one example, the foamable liquid composition includes from 30 to 80 percent water, by weight. Preferably the foamable liquid composition comprises from 30 to 60 percent water, by weight. Preferably, the foamable liquid composition further includes an acid at a concentration of from 0.5 to 5 percent, by weight, of the foamable liquid composition. The acid may be selected from the group consisting of an inorganic acid, an organic acid with chain length of eight carbons or less and mixtures thereof. A preferred foamable liquid composition includes from 1 to 4 percent, by weight, lactic acid, from 1 to 50, preferably from 5 to 30 percent, by weight, of an alcohol having from one to four carbon atoms, such as methanol, ethanol, propanol and mixtures thereof, and one or more water soluble solvents, such as butylene glycol, glycerin, polyglycerin, ethylene glycol, and propylene glycol. Preferably, said alcohol is ethanol and preferably said water soluble solvent is propylene glycol in an amount of from 1 to 20 percent, by weight, and more preferably from 5 to 15 percent, by weight, of the foamable liquid composition. The liquid foam composition according to the invention contains at least one surfactant. Preferably, the foamable liquid composition comprises from 0.1 to 5 percent, by weight, of a surfactant, more preferably from 0.2 to 1 percent, by weight of a surfactant. Suitable surfactants have emulsifying, solvating, and foam-forming or foam-stabilizing properties; are preferably nonionic; and have a hydrophilic lipophilic balance (HLB) value of greater than about fifteen. In particular, the surfactant oleth-20 is preferred in an amount of from 0.1 to 5 percent, by weight, of the foamable liquid composition and more preferably from 0.2 to 1 percent, by weight, of the foamable liquid composition.

Other surfactants optionally used with the present formulation include, but are not limited to: any combination of anionic, cationic, non-ionic, or amphoteric surfactants with an HLB value of greater than fifteen.

Optionally, the foam formed is maintained with a foam stabilizer. In the treatment of the human scalp for androgenic alopecia the maintenance of foam is important to allow a known and suitable period of contact of the minoxidil and bimatoprost with the scalp. The foam stabilizer is preferably included in the foamable liquid composition in an amount of from 0.05 to 0.5 percent, and more preferably from 0.1 to 0.5 percent, by weight.

In particular, the stabilizer includes lauryl glucoside in an amount of from 0.05 and 0.5% by weight and more preferably from 0.1 to 0.5 percent, by weight, of the foamable liquid composition.

Other optional foam stabilizers used with the present liquid composition include, but are not limited to: fatty amine oxides, a quaternary amines, or a cellulose derivatives, such as methyl cellulose and ethyl cellulose.

The liquid composition can be sprayed on the scalp daily to stimulate the growth of hair.

Example 23

A gel comprising bimatoprost and minoxidil in a pharmaceutically-acceptable solvent comprising propylene glycol and alcohol and a cross-linked acrylic polymer thickening agent such as a Carbomer, e.g. Carbomer 934P, is prepared as described below. The cross-linked acrylic polymer thickening agent is neutralized with a neutralizing agent such as diisopropanolamine.

The gel comprises from 0.0000001% to 10% bimatoprost and from 0.001% to 10% minoxidil, by weight. More preferably said gel comprises from 0.01% to 0.5% bimatoprost and from 1% to 5% minoxidil, by weight, most preferably said composition comprises 0.03% bimatoprost and 5% minoxidil, by weight.

Said pharmaceutically acceptable solvent is selected from the group consisting of ethanol, propanol, butanol, propylene glycol, dipropylene glycol, hexylene glycol, 1,3-butylene glycol, PEG-200, PEG-400, glycerol and mixtures thereof.

Most preferably, said solvent is selected from the group consisting of ethanol and isopropanol.

Alternatively, said solvent selected from the group consisting of propylene glycol, dipropylene glycol, hexylene glycol, 1,3-butylene glycol, PEG-200, PEG-400, and glycerol.

Most preferably, said solvent is propylene glycol.

In a second alternative embodiment of the invention, said solvent comprises a mixture comprising a first solvent selected from the group consisting of ethanol, propanol and butanol and a second solvent selected from the group consisting of propylene glycol, dipropylene glycol, hexylene glycol, 1,3-butylene glycol, PEG-200, PEG-400, and glycerol.

Preferably, in said second alternative embodiment of the invention, said solvent comprises a mixture of ethanol and propylene glycol.

The gel further comprising a neutralizing agent, wherein said neutralizing agent may be selected from the group consisting of ammonium hydroxide, arginine, 2-amino-2-methyl-1-propanol, dimethanolamine, dibutanolamine, diisobutanolamine, tributanolamine, triisobutanolamine, tri-sec-butanolamine, tripropylamine, ethanolamine, diethanolamine, triethanolamine, PEG-15 cocamine, diisopropanolamine, methylethanolamine, diisopropylamine, dipropylenetriamine, tromethamine, isopropylamine ethylene diamine, triisopropanolamine, tetrahydroxypropyl ethylenediamine, trimethamine, 2-aminobutanol, aminoethyl propanediol, aminomethyl propanediol, aminomethyl propanol, sodium hydroxide, and potassium hydroxide.

A pharmaceutically elegant gel comprising minoxidil and bimatoprost is prepared by mixing the below-described mixtures:

| Ingredient | % w/w |
|---|---|
| Part I | |
| Purified water USP | q.s. 100 |
| Carbopol ® 934P | 0.45 |
| Part II | |
| Bimatoprost | 0.03 |
| Minoxidil | 5 |
| propylene glycol USP | 10 |
| alcohol USP | 13 |
| diisopropanolamine NF | 0.45 |
| Part III | |
| alcohol USP | 27 |

What is claimed is:

1. A method for promoting and enhancing chest hair growth in an adolescent human male or adult human male who has a normal level of circulating total serum testosterone (T) androgen hormone that is within a normal physiologic reference range, wherein said human male is unable to grow chest hair, comprising topically administering an effective amount of a pharmaceutically acceptable formulation of dihydrotestosterone (DHT) to a targeted skin surface area of the human male, and wherein said targeted skin surface area has sparse mature terminal hair growth to promote and enhance growth of mature terminal hair at the targeted skin surface area, wherein said adult human male does not have a genetically determined lower level of intracellular 5 alpha reductase and does not have a genetically determined lower number of androgen receptors.

2. The method as claimed in claim 1, in which said administration is repeated daily until desired hair growth results.

3. The method as claimed in claim 1, wherein said formulation is selected from the group comprising topical liquids, lotions, creams, ointments, solutions, gels, foams, aerosols, or sprays.

4. The method as claimed in claim 1, in which said formulation is formulated to deliver said dihydrotestosterone (DHT) to the hair follicles and hair follicle bulb matrices of hair in said target skin area.

5. The method as claimed in claim 1, in which said formulation is formulated to deliver said dihydrotestosterone (DHT) to the hair follicle and the mesenchymal dermal papilla cells of said hair follicle in said target skin area.

6. The method as claimed in claim 4, in which said formulation is adsorbed onto or into a hair shaft and drawn by capillary action to said hair follicle bulb and other parts of the hair follicle.

7. The method as claimed in claim 4, in which said formulation crosses the surface of the skin and is transported to said hair follicle bulb matrix by trans-epidermal diffusion or by transdermal diffusion.

8. The method as claimed in claim 7, in which said formulation additionally comprises one or more dermal penetration enhancement agents.

9. The method as claimed in claim 8, in which said dermal penetration enhancement agent comprises one or more alcohols selected from the group consisting of methanol, ethanol, propanol, isopropanol and isopropyl myristate.

10. The method as claimed in claim 8, in which the concentration of said dermal penetration enhancement agent is no greater than a concentration sufficient to enhance dihydrotestosterone (DHT) penetration to layers of dermis containing hair follicle bulb matrices.

11. The method as claimed in claim 10, in which said dermal penetration enhancement agent concentration is formulated so as to deliver said dihydrotestosterone (DHT) to said hair follicle bulb matrices, but that said dihydrotestosterone (DHT) is not significantly absorbed into the systemic circulation.

12. The method as claimed in claim 1, wherein said dihydrotestosterone (DHT) concentration is in a range of from about 0.5% to about 25%, weight to weight.

13. The method as claimed in claim 1, wherein said dihydrotestosterone (DHT) concentration is in a range of from about 0.5% to about 25%, weight to volume.

14. The method as claimed in claim 1, wherein said dihydrotestosterone (DHT) concentration is in a range of from about 0.5% to about 25%, volume to volume.

15. The method as claimed in claim 1, in which said dihydrotestosterone (DHT) formulation additionally comprises sodium chloride, dibasic sodium phosphate, citric acid, a thickening agent, or pharmaceutically acceptable purified water.

* * * * *